United States Patent
Baraszu et al.

(10) Patent No.: US 9,395,327 B2
(45) Date of Patent: Jul. 19, 2016

(54) SYSTEMS AND METHODS TO PROTECT AGAINST OVER-DISCHARGE IN A BATTERY SYSTEM

(71) Applicant: GM GLOBAL TECHNOLOGY OPERATIONS LLC, Detroit, MI (US)

(72) Inventors: Robert C. Baraszu, Dearborn, MI (US); Kurt M. Johnson, Brighton, MI (US); Zachary D. Bylsma, Rochester Hills, MI (US); Damon R. Frisch, Troy, MI (US); Wei Liu, Warren, MI (US); David S. Maxwell, Madison Heights, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 796 days.

(21) Appl. No.: 13/690,886

(22) Filed: Nov. 30, 2012

(65) Prior Publication Data

US 2014/0152317 A1    Jun. 5, 2014

(51) Int. Cl.
*G01N 27/416* (2006.01)
*H01M 10/48* (2006.01)

(52) U.S. Cl.
CPC ............ *G01N 27/416* (2013.01); *H01M 10/482* (2013.01); *H01M 2220/20* (2013.01)

(58) Field of Classification Search
CPC .......... H01M 2220/20; H01M 10/482; G01R 31/3658; Y02E 60/12; H02J 2007/004
USPC .......... 320/132, 134, 162; 324/427, 433, 434
See application file for complete search history.

(56) References Cited

U.S. PATENT DOCUMENTS

2009/0315519 A1* 12/2009 Izumi et al. .................. 320/134

* cited by examiner

*Primary Examiner* — Edward Tso
*Assistant Examiner* — Aaron Piggush
(74) *Attorney, Agent, or Firm* — Phillips Ryther & Winchester; Jared L. Cherry (57) ABSTRACT

A battery system may include a plurality of subdivisions, such as battery cells or sub-packs. A measurement system configured to determine a subdivision electrical parameter associated with each of a plurality of subdivisions. A battery control may identify a subdivision satisfying a criterion based on the plurality of subdivision electrical parameters. According to some embodiments, the battery control system may determine a ratio of the subdivision electrical parameter of the identified subdivision to the electrical parameter of the battery pack. The ratio may be used to scale the electrical parameter associated with the battery pack by the ratio. According to other embodiments, the subdivision electrical parameter associated with the identified subdivision may be provided to a battery state estimation system. The scaled electrical parameter or the electrical parameter associated with the identified subdivision may be used by a battery state estimation system to generate an estimated battery state.

18 Claims, 5 Drawing Sheets

SYSTEMS AND METHODS TO PROTECT AGAINST OVER-DISCHARGE IN A BATTERY SYSTEM

TECHNICAL FIELD

The systems and methods disclosed herein relate to protecting against over-discharge of a battery system. More specifically, the systems and methods of the present disclosure relate to monitoring individual subdivisions of a battery system and implementing controls to prevent over-discharge of individual subdivisions of the battery system.

BACKGROUND

Passenger vehicles often include electric batteries for operating a vehicle's electrical and drivetrain systems. For example, vehicles commonly include a 12V lead-acid automotive battery configured to supply electric energy to vehicle starter systems (e.g., a starter motor), lighting systems, and/or ignition systems. In electric, fuel cell ("FC"), and/or hybrid vehicles, a high voltage ("HV") battery system may be used to power electric drivetrain components of the vehicle (e.g., electric drive motors and the like).

Battery discharge may terminate when the battery is depleted or at a threshold established by a battery control system. The threshold for terminating further discharge may be based upon monitoring the voltage or other parameters of the battery as a whole. Failure to restrict further discharge of the battery below an over-depletion threshold may result in battery system inefficiencies, degradation, permanent damage and/or a shortened usable lifespan.

SUMMARY

A battery system according to various embodiments of the present disclosure may include a plurality of subdivisions, such as battery cells or sub-packs. Over extended periods of use, different battery subdivisions may develop differences in capacities, states of charge, discharge rates, impedances, and/or voltages. Consistent with embodiments disclosed herein, a battery system may include a measurement system configured to determine a subdivision electrical parameter associated with each of a plurality of subdivisions. A battery control system may identify a subdivision satisfying a criterion based on the plurality of subdivision electrical parameters. For example, the systems and methods disclosed herein may detect a battery subdivision satisfying certain criteria (e.g., the weakest or lowest capacity subdivision) within a battery pack for the purpose of utilizing that subdivision's electrical characteristics to estimate battery control parameters.

According to various embodiments, the weakest subdivision may refer to the cell having the lowest electrical storage capacity, the highest electrical resistance, or other characteristic depending on the battery chemistry. In some instances, the subdivision having the highest electrical resistance is also the cell having the lowest capacity, while in other cases this relation does not hold. Accordingly, various embodiments may select one or more battery subdivisions meeting a specified criteria (e.g., lowest capacity, highest electrical resistance, lowest voltage, lowest current, etc.). Embodiments that identify the weakest subdivision within a battery and utilize the electrical characteristics of the weakest subdivision to estimate battery control parameters may consequently protect weak cells from over-discharge and the attendant permanent damage.

According to some embodiments, the battery control system may determine a ratio of the subdivision electrical parameter of the identified subdivision to the electrical parameter of the battery pack. The ratio may be used to suitably scale the electrical parameter associated with the battery pack (e.g., scale the electrical parameter by the ratio). According to other embodiments, the subdivision electrical parameter associated with the identified subdivision may be provided to a battery state estimation system. The scaled electrical parameter or the electrical parameter associated with the identified subdivision may be used by a battery state estimation system to generate an estimated battery state.

BRIEF DESCRIPTION OF THE DRAWINGS

Non-limiting and non-exhaustive embodiments of the disclosure are described, including various embodiments of the disclosure with reference to the figures, in which.

DETAILED DESCRIPTION

A detailed description of systems and methods consistent with embodiments of the present disclosure is provided below. While several embodiments are described, it should be understood that the disclosure is not limited to any one embodiment, but instead encompasses numerous alternatives, modifications, and equivalents. In addition, while numerous specific details are set forth in the following description in order to provide a thorough understanding of the embodiments disclosed herein, some embodiments can be practiced without some or all of these details. Moreover, for the purpose of clarity, certain technical material that is known in the related art has not been described in detail in order to avoid unnecessarily obscuring the disclosure.

The embodiments of the disclosure will be best understood by reference to the drawings, wherein like parts may be designated by like numerals. The components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments of the disclosure. In addition, the steps of a method do not necessarily need to be executed in any specific order, or even sequentially, nor need the steps be executed only once, unless otherwise specified.

Battery packs for hybrid and purely electric vehicles may include a plurality of subdivisions. For example, a vehicle battery system may include a battery pack that comprises one or more sub-packs or battery cells. The term subdivision, as used herein, may refer to either a sub-pack or a battery cell, or to a plurality of sub-packs or battery cells that together constitute a battery pack.

A battery having a plurality of subdivisions may provide efficiencies in packaging, manufacturability, and serviceability. In battery packs comprising multiple subdivisions, each subdivision may be individually replaceable. Individual subdivisions may fail or require replacement for a variety of reasons. In a battery system in which individual subdivisions are not individually replaceable, when one or more subdivisions fails or requires replacement, it may be necessary to replace the entire battery. The cost of replacing the entire battery may significantly exceed the cost of replacing only one or more subdivisions. Accordingly, significant cost savings may be realized where a problem with a battery may be remedied by replacing only a single subdivision rather than replacing the entire battery.

As a result of replacement of one or more subdivisions, variations among subdivisions in a battery at the time of manufacture, or other issues, individual subdivisions may exhibit different electrical characteristics. Such characteristics may include differences in energy storage capacity, voltage, current, impedance, and the like. For example, in a circumstance in which a subdivision is replaced in a battery after considerable use, the newly replaced subdivision may have greater capacity than other subdivisions, whose capacity may have diminished over time and as a result of use.

A control system may monitor the condition of a battery while in use in order to prevent over-discharge of the battery and/or over-discharge of one or more individual subdivisions. Over-discharge of a battery may result in permanent damage to the battery and, accordingly, mitigating and/or preventing over-discharge of a battery is desirable. Further, given that individual subdivisions in a battery may exhibit differences in capacity, some subdivisions may become over-discharged before other sections are over-discharged and even before the battery as a whole is over-discharged. Individual monitoring and protection against over-discharge of individual subdivisions may be of greater concern after one or more subdivisions in a battery are replaced because the newly replaced subdivision may be able to store greater amounts of electrical energy, and thus, other subdivisions may become over-depleted before the newly replaced subdivision.

The systems and methods disclosed herein may detect a battery subdivision satisfying certain criteria (e.g., the lowest capacity subdivision, highest electrical resistance, etc.) within a battery pack for the purpose of utilizing that subdivision's electrical characteristics to estimate battery control parameters. Embodiments that identify a weak or low capacity subdivision within a battery and utilize the electrical characteristics of the weak subdivision in order to estimate battery control parameters may consequently protect weak cells from over-discharge and resulting damage. Such damage may further compound the reduction in the amount of energy a low-capacity subdivision may be able to store. Accordingly, the capacity of an already lower-capacity subdivision may degrade at an accelerated rate with respect to other subdivisions that have an average or above-average energy storage capacity if the lower-capacity subdivision is damaged from over-discharge.

According to one embodiment, a battery control system may rely on the measured voltage across the entire battery pack and synchronized current measurements. Such an embodiment may be well suited for battery packs whose individual subdivisions are of similar capacity, such as a new pack or one whose cells have aged at the same or similar rates.

The battery control system, according to some embodiments, may rely on voltage measurements that are approximately synchronized with battery pack current measurements. It may be difficult to synchronize each measurement, since it may take a significant amount of time to sample each of the many cell voltages. In some embodiments the number of cells to be measured may be on the order of 100. One solution to this problem is to design hardware to enable synchronization between the current of the battery pack as a whole and the voltage of a weak subdivision. For example, one option is to identify not a weak cell, but a weak sub-pack, which may contain a plurality of cells. Synchronized subdivision voltage and current measurements are feasible; however, such a solution may increase the cost and complexity of the battery system by requiring additional hardware. Certain embodiments according to the present disclosure may be implemented using software, and accordingly, may be incorporated into existing battery systems with minimal or no additional hardware.

Various systems and methods disclosed herein may be able to closely estimate the voltage of the weakest cell or sub-pack in a battery while maintaining sufficient synchronization between that estimated voltage and pack current. This resulting estimation of a weak subdivision's voltage may be sufficient for the battery control system to properly function.

According to another embodiment, a battery control system may measure electrical parameters associated with individual subdivisions. Monitoring may occur while the battery is charging (e.g., is plugged into a power source) or while the battery is discharging (e.g., electrical energy is being drawn from the battery to drive an electrical vehicle). The battery control system may identify the voltage of a weak subdivision in the battery and the average voltage of the battery pack. In certain embodiments, a weak subdivision may be the weakest subdivision included in a battery system. A ratio of the voltage of the weak subdivision to the average voltage of the battery pack (e.g., the average voltage of the battery) may be used to scale the average voltage of the battery. The scaled average voltage may then be provided to a battery state estimation system in order to generate an estimated battery state. The estimated battery state may include an estimated state of charge associated with one or more individual subdivisions.

Figure 1:
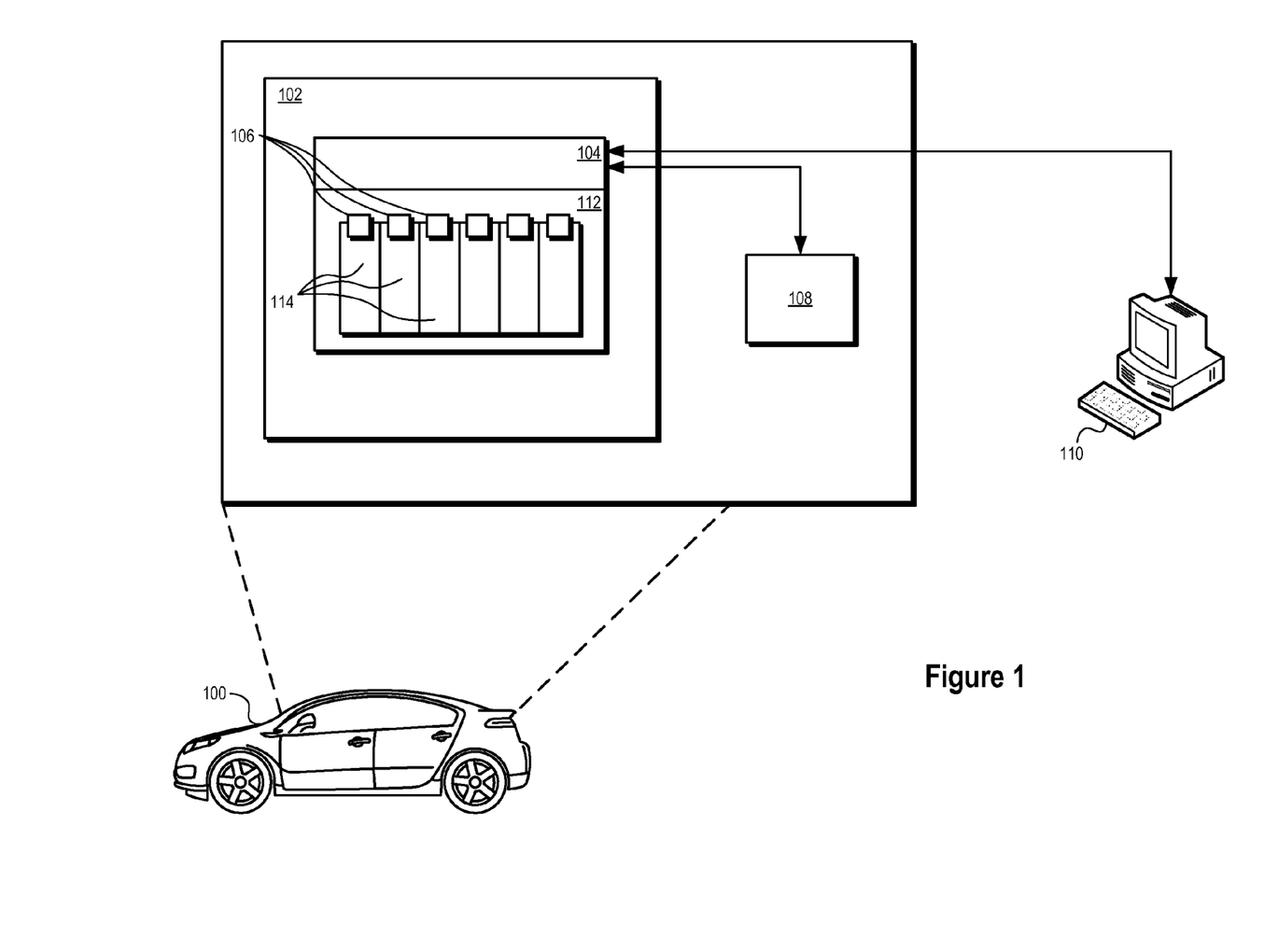
FIG. 1 illustrates an exemplary system for balancing a battery system in a vehicle consistent with embodiments disclosed herein.

FIG. 1 illustrates an exemplary system control system in a vehicle 100 consistent with embodiments disclosed herein. The vehicle 100 may be a motor vehicle, a marine vehicle, an aircraft, and/or any other type of vehicle, and may include an internal combustion engine ("ICE") drivetrain, an electric motor drivetrain, a hybrid engine drivetrain, an FC drivetrain, and/or any other type of drivetrain suitable for incorporating the systems and methods disclosed herein. The vehicle 100 may include a battery system 102 that, in certain embodiments, may be an HV battery system. The HV battery system may be used to power electric drivetrain components (e.g., as in an electric, hybrid, or FC power system). In further embodiments, the battery system 102 may be a low voltage battery (e.g., a lead-acid 12V automotive battery) and may be configured to supply electric energy to a variety of vehicle 100 systems including, for example, vehicle starter systems (e.g., a starter motor), lighting systems, ignition systems, and/or the like.

The battery system 102 may include a battery control system 104. The battery control system 104 may be configured to monitor and control certain operations of the battery system 102. For example, the battery control system 104 may be configured to monitor and control charging and discharging operations of the battery system 102. In certain embodiments, the battery control system 104 may be communicatively coupled with one or more sensors 106 (e.g., voltage sensors, current sensors, and/or the like, etc.) and/or other systems configured to enable the battery control system 104 to monitor and control operations of the battery system 102. For example, sensors 106 may provide battery control system 104 with information used to estimate a state of charge of the battery system 102 and/or its constituent components. The battery control system 104 may further be configured to provide information to and/or receive information from other systems included in the vehicle 100. For example, the battery control system 104 may be communicatively coupled with an internal vehicle computer system 108 and/or an external computer system 110 (e.g., via a wireless telecommunications system or the like). In certain embodiments, the battery control system 104 may be configured, at least in part, to provide information regarding the battery system 102 to a user of the vehicle 100, vehicle computer system 108, and/or external computer system 110. Such information may include, for example, battery state of charge information, battery operating time information, battery operating temperature information, and/or any other information regarding the battery system 102.

The battery system 102 may include one or more battery packs 112 suitably sized to provide electrical power to the vehicle 100. Each battery pack 112 may include one or more subdivisions 114. The subdivisions 114 may comprise sub-packs, each of which may comprise one or more battery cells utilizing any suitable battery technology. Suitable battery technologies may include, for example, lead-acid, nickel-metal hydride ("NiMH"), lithium-ion ("Li-Ion"), Li-Ion polymer, lithium-air, nickel-cadmium ("NiCad"), valve-regulated lead-acid ("VRLA") including absorbed glass mat ("AGM"), nickel-zinc ("NiZn"), molten salt (e.g., a ZEBRA battery), and/or other suitable battery technologies.

Each subdivision 114 may be associated with a sensor 106 configured to measure one or more electrical parameters (e.g., voltage, current, impedance, state of charge, etc.) associated with each battery subdivision 114. Although FIG. 1 illustrates separate sensors 106 associated with each battery section 114, in some embodiments a sensor configured to measure various electrical parameters associated with a plurality of subdivisions 114 may also be utilized. The electrical parameters measured by sensor 106 may be provided to battery control system 104. Using the electrical parameters, battery control system 104 and/or any other suitable system may coordinate the operation of battery system 102.

In certain embodiments, information regarding battery balancing operations may be provided by battery control system 104 to vehicle computer system 108, and/or external computer system 110. For example, an indication regarding differences between various subdivisions 114 may be provided. Such differences may include, for example, variations in the voltage of each subdivision 114, differences in the amount of current that can be sourced from each subdivision 114, differences in the capacity of each subdivision 114, etc. With this information, a user of the vehicle 100 and/or external computer system 110 may diagnose potential problems with battery system 102. Subdivisions 114 exhibiting undesirable characteristics may be replaced in order to prolong the useful life of battery system 102 as a whole.

Figure 2A:
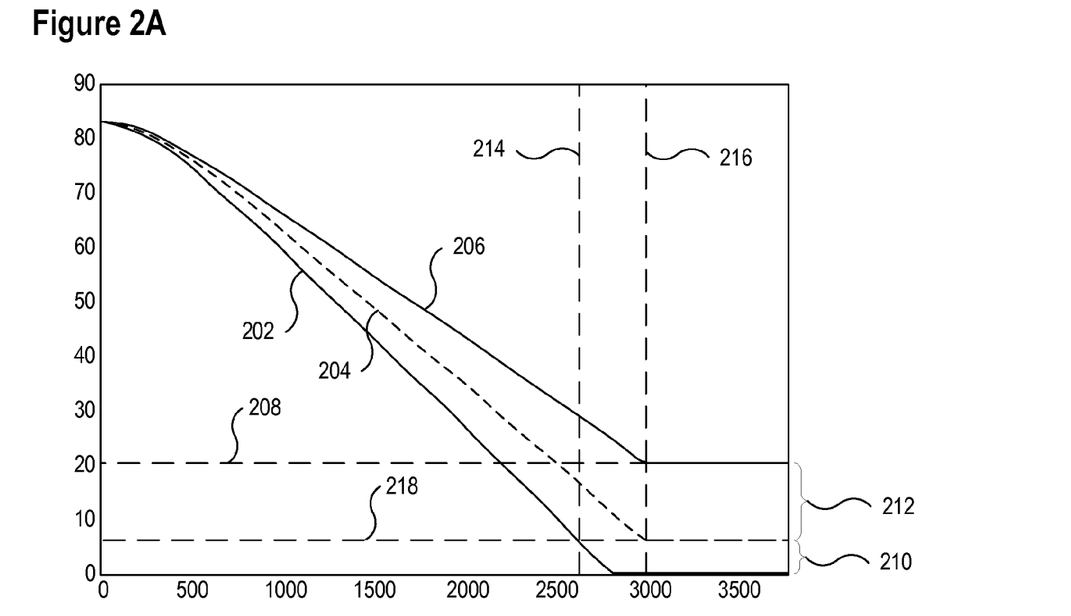
FIG. 2A is a graph illustrating the state of charge over time of an exemplary high-capacity subdivision and an exemplary low-capacity subdivision, in which a battery control system utilizes an average state of charge of the battery to determine when to prevent further discharge from the battery.

FIG. 2A is a graph showing the state of charge over time of a high-capacity subdivision, a low-capacity subdivision, and an average state of charge of a battery controlled by a battery control system that utilizes the average state of charge of the battery to determine when to prevent further discharge from the battery. Time in minutes is shown along the x-axis and a state of charge expressed as a percentage is illustrated along the y-axis.

Line 202 illustrates the state of charge of a low-capacity cell and line 206 illustrates the state of charge of a high-capacity cell. Line 204 illustrates the average state of charge of a battery including the high-capacity subdivision, the low-capacity subdivision, and a plurality of additional subdivisions. As shown, the average state of charge of the battery (i.e., line 204) is between the high capacity subdivision 206 and the low-capacity subdivision 202.

A threshold 208 may be defined as a point at which further depletion from the battery is restricted. According to some embodiments, threshold 208 may be above, although near, the state of charge level at which over-depletion may occur. The time at which the threshold 208 is reached depends on which parameter is evaluated. For example, according to the embodiment illustrated in FIG. 2A, a battery control system may rely on the average state of charge of the battery (i.e., line 204). According to the illustrated embodiment, the average state of charge reaches the threshold 208 at time 216; however, the state of charge of the low-capacity cell reached the threshold at time 214. At time periods after time 214, low-capacity cell (i.e., line 202) may experience damage as a result of becoming over-discharged. The average state of charge (i.e., line 204) at time 216 exceeds the state of charge of the low-capacity subdivision (i.e., line 202) by a margin designated by reference number 210. Similarly, the state of charge of the high-capacity subdivision (i.e., line 206) exceeds the average state of charge (i.e., line 204) by a margin designated by reference number 212. As shown, there may be significant differences between the state of charge of the high-capacity subdivision, the low-capacity subdivision and the average subdivision. The differences may be accentuated when the battery is deeply discharged.

Figure 2B:
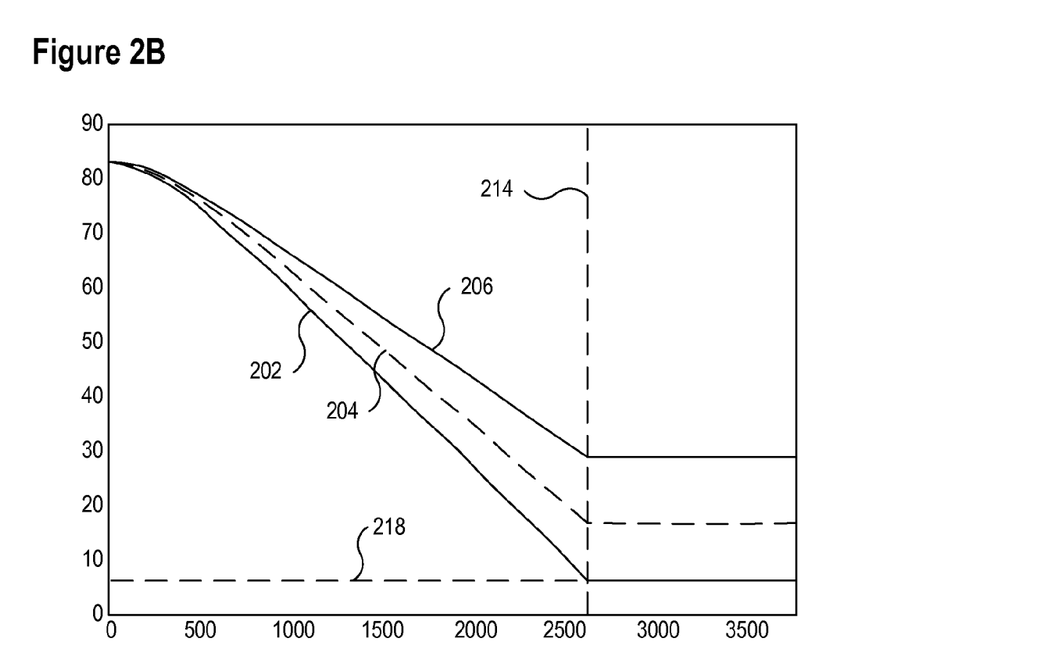
FIG. 2B is a graph illustrating the state of charge over time of an exemplary high-capacity subdivision and an exemplary low-capacity subdivision, in which a battery control system utilizes the state of charge of the low-capacity subdivision to determine when to prevent further discharge from the battery.

FIG. 2B is a graph showing the state of charge over time of a high-capacity subdivision, a low-capacity subdivision, and an average state of charge of a battery controlled by a battery control system that utilizes the low-capacity subdivision state of charge of the battery to determine when to prevent further discharge from the battery. In contrast to FIG. 2A, the low-capacity subdivision does not fall below threshold 218, and accordingly, the low-capacity subdivision does not become over-discharged. Preventing over-discharge of the low-capacity subdivision (i.e., line 202) may help to prevent damage to the low-capacity cell and to extend the useful life of the battery. Preventing further discharge based on the weakest subdivision may ensure that no over-discharge occurs in any subdivisions since all other subdivisions have a state of charge that is greater than the weakest subdivision.

Figure 3A:
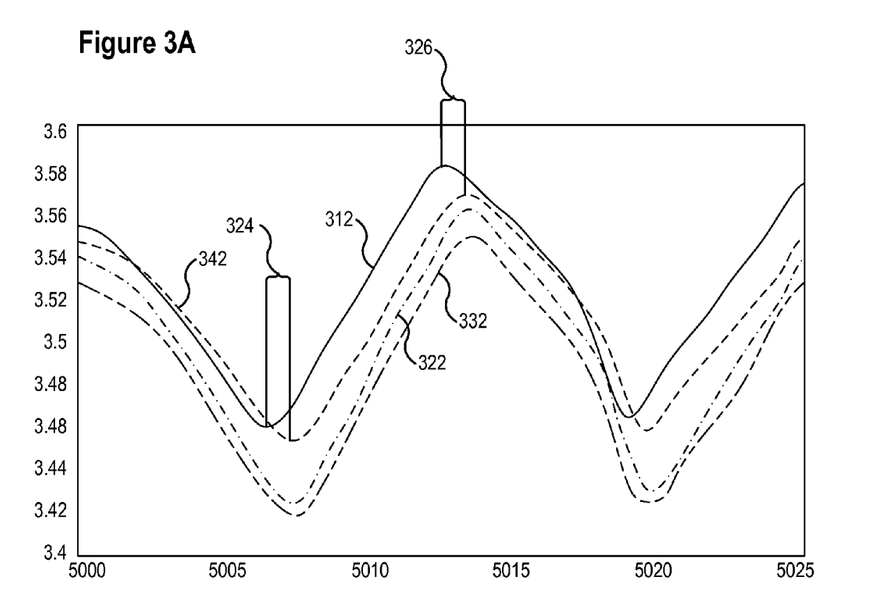
FIG. 3A is a graph over time illustrating a battery pack voltage scaled to a cell-level, a voltage of a weakest cell or average voltage of the weakest subdivision, an average voltage of all cells in the battery pack, and a voltage scaled by the ratio of the weakest cell or subdivision voltage to the average voltage of all cells in the pack consistent with embodiments disclosed herein.

FIG. 3A is a graph over time illustrating a variety of voltages associated with a battery system. Scaled pack voltage 312 corresponds to a battery pack voltage scaled to a cell level (i.e., the total battery voltage divided by the number of cells in the battery). As described below, the scaled pack voltage 312 may be time synchronized with battery pack current. Voltage 332 corresponds to the voltage of a weak cell in the battery system, and voltage 342 corresponds to the average voltage of all cells in the battery pack. According to alternative embodiments, the voltage of the weakest cell 332 may represent an average voltage of a plurality of cells.

Each of voltages 312, 332, 342 may vary over time depending upon the current drawn from the battery at a particular time. According to the illustrated embodiment, the amount of current drawn from a battery varies over time, thus leading to the peaks and valleys shown in FIG. 3A.

FIG. 3A also illustrates an adjusted pack electrical parameter 322 that is calculated by scaling and time shifting the scaled pack voltage 312 based upon the ratio of the weakest cell 332 and the average voltage of all cells in the battery pack 342. A time delay 324 may be measured between a local minimum of the scaled pack voltage 312 and a corresponding local minimum voltage of the average voltage of all cells 342. According to some embodiments, a time delay 326 between a local maximum of scaled pack voltage 312 and a corresponding local maximum voltage of the average voltage of all cells 342 may also be utilized to determine a time delay. Voltage 312 may be shifted in time by the time delay (e.g., time delay 324 or 326) to achieve synchronization of the battery pack voltage and current and the voltage of the weak cell or average voltage of the weak subdivision.

In FIG. 3A, voltages 332 and 342 are measured values, and may be used to calculate a scaling ratio using Eq. 1.

$$\text{Ratio} = \frac{\text{Weak Cell Voltage}}{\text{Average of all Cell Voltages}} \quad \text{Eq. 1}$$

The ratio may be used to calculate scaled voltage 322 using Eq. 2.

$$\text{Scaled Voltage} = \text{Ratio} * \text{Measured Voltage per Cell} \quad \text{Eq. 2}$$

Using Eq. 1 and Eq. 2 to calculate the scaled voltage may prevent over discharge of the weak cell.

Figure 3B:
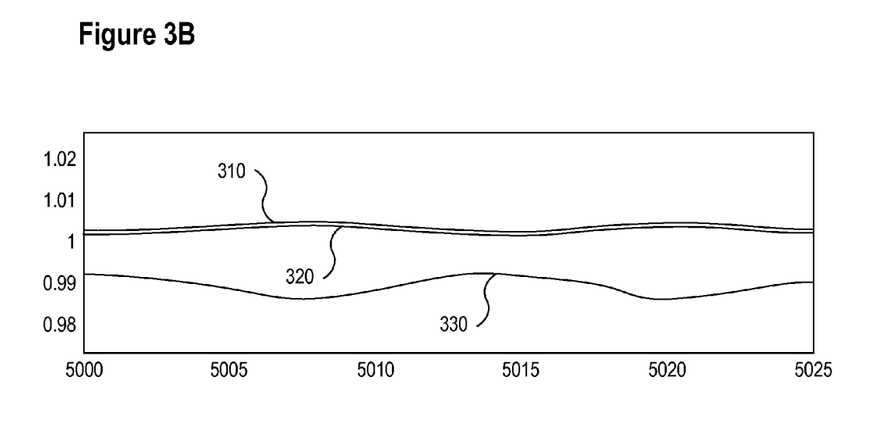
FIG. 3B is a graph over time illustrating the ratios of voltage over time of two exemplary high capacity cells or subdivisions and an exemplary low capacity cell or subdivision to the average voltage of all cells or subdivisions of the battery pack consistent with embodiments disclosed herein.

FIG. 3B shows over time ratios between measurements of three battery cells in a battery and a measured battery voltage per cell. Ratios 310 and 320 are greater than 1 and, accordingly, the sections corresponding to ratios 310 and 320 correspond to cells that have a greater-than-average voltage. Ratio 330 has a value that is less than 1 and, accordingly, the battery section corresponding to ratio 330 corresponds to a cell having a less-than-average voltage. In the illustrated scenario, the battery section corresponding to ratio 330 is a weak section, and accordingly, may be used in the numerator of Eq. 1 to calculate a ratio that can be used to determine a scaled voltage.

According to one embodiment, a battery control system may identify ratio 330 as corresponding to a cell having a specific characteristic (e.g., lowest capacity, highest electrical resistance, etc.). Accordingly, the battery control may scale the pack voltage per cell in the battery pack by the ratio 330. In the alternative, the total voltage of the battery (i.e., the sum of the voltage of each cell) may be scaled by the ratio 330.

The battery control system may be configured to communicate the scaled voltage to a battery estimation system. The battery estimation system may receive various parameters and may utilize as inputs one or more measured electrical characteristics associated with the battery system. According to one embodiment, the measurements of electrical parameters may include a voltage of a battery terminal and a current drawn from the battery. According to other embodiments, other parameters may be measured including, for example, the impedance of the battery (e.g., real and/or imaginary). Measurements of electrical characteristics associated with the battery may be acquired using appropriate sensors, such as voltage sensors, current sensors, and/or impedance sensors.

Figure 4:
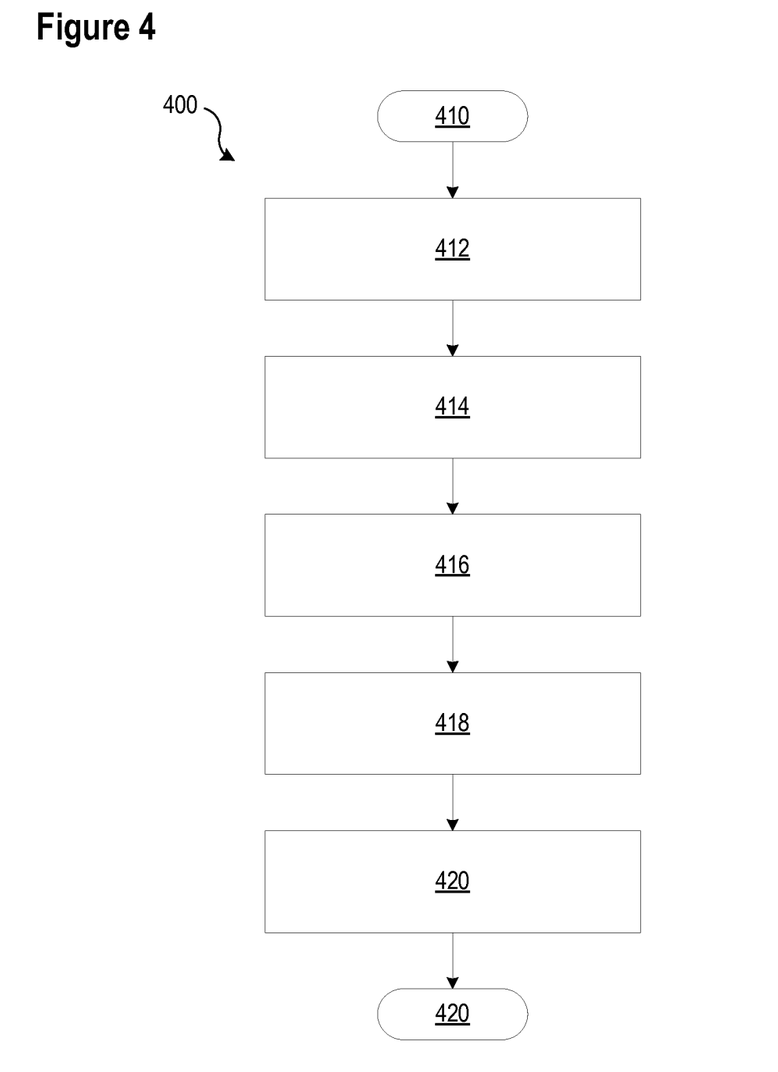
FIG. 4 illustrates a flow chart of a method for protecting against over-discharge of a vehicle battery system consistent with embodiments disclosed herein.

FIG. 4 illustrates a flow chart of an exemplary method 400 for protecting against over-discharge of a vehicle battery system consistent with embodiments disclosed herein. Method 400 may begin at 410, and at 412 may acquire subdivision voltage and current measurements. According to some embodiments, the measurements may be acquired synchronously. In embodiments in which voltage and current measures are acquired synchronously, the process of synchronizing the voltage and current measurements described below at 418 may not be necessary. The voltage measurements, current measurements, and/or other measurements or calculations may be used, at 414, to estimate one or more battery parameters and/or battery states. According to some embodiments, the battery state to be estimated relates to the state of charge of the battery and the battery's individual subdivisions (e.g., sub-packs and/or cells). At 416, a weak subdivision of the battery may be identified using the measurements acquired at 412.

The battery control system, according to some embodiments, may rely on voltage measurements that are approximately synchronized with battery pack current measurements. It may be difficult to synchronize each measurement, since it may take a significant amount of time to sample each of the many cell voltages. In some embodiments the number of cells to be measured may be on the order of 100. One solution to this problem is to design hardware implementing method 400 in a way that enables synchronization between pack current and a weak subdivision's voltage. For instance, one option is to identify not the weakest cell, but the weakest subdivision. While synchronized subdivision voltage and current measurements can be made consistent with embodiments disclosed herein, such a solution may increase the cost and complexity of the battery system by requiring additional hardware. Certain embodiments according to the present disclosure may be implemented using software, and accordingly, may be incorporated into existing battery systems with minimal or no additional hardware.

Various systems and methods disclosed herein may be configured to closely estimate the voltage of a weak cell or subdivision (e.g., the weakest cell or subdivision) in a battery while maintaining sufficient synchronization between that estimated voltage and pack current. This resulting estimation of the weak subdivision's voltage may be sufficient for the battery control system to properly function.

If necessary, voltage and current measurements may be synchronized at 418. According to one embodiment, the process of synchronizing the voltage and current measurements may include measuring a time delay between a maximum or minimum value of the pack voltage per cell and the corresponding maximum or minimum value of an average voltage of all subdivisions in a battery. According to some embodiments, the delay may be determined using the absolute value of the relevant voltages. The time delay may be utilized by a battery state estimation system in generating an estimate of the state of charge of the battery pack.

At 420, the synchronized voltage and current measurements associated with the weakest subdivision may be utilized by a battery state estimator. According to some embodiments, the battery state estimator may estimate a state of charge associated with the subdivision. For example, the battery state estimator may estimate a state of charge associated with a weakest subdivision of the battery system. A battery control system may utilize the estimated state of charge in order to control, among other things, the discharge from the battery. The battery control system may, for example, restrict further discharge from a battery in order to prevent against over-discharging the weakest cell and/or sub-pack in the battery.

Figure 5:
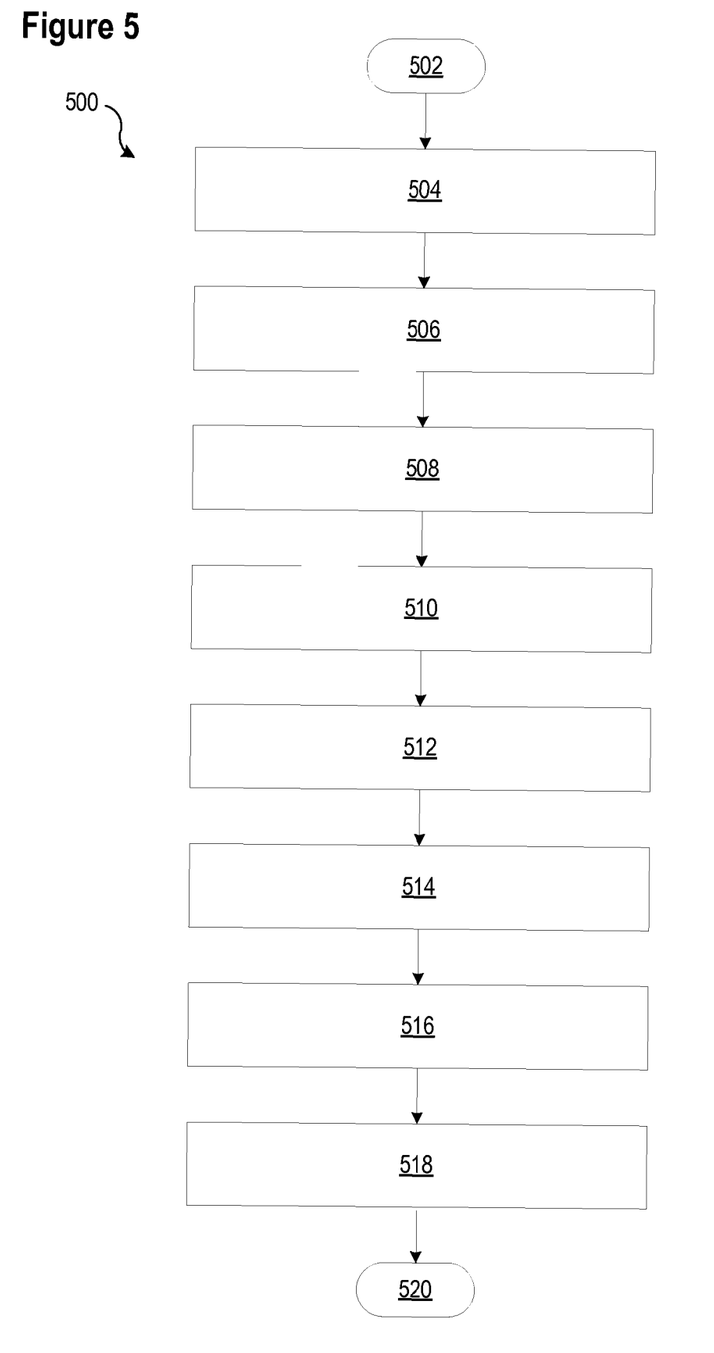
FIG. 5 illustrates a flow chart of another method for protecting against over-discharge of a vehicle battery system consistent with embodiments disclosed herein.

FIG. 5 illustrates a flow chart of an exemplary method 500 for protecting against over-discharge of a vehicle battery system consistent with embodiments disclosed herein. At 502, method 500 may begin. At 504, an electrical parameter associated with each of the plurality of subdivisions in the battery may be determined. Determining the electrical parameter may include measuring the electrical parameter and/or receiving the electrical parameter from another system via a communications interface.

One or more subdivisions satisfying a criterion may be identified at 506. According to various embodiments, the criterion may be set to identify subdivisions exhibiting an electrical characteristic (e.g., an electrical storage capacity, a voltage, an ability to source current, etc.) below a threshold level.

Method 500 may determine or calculate at 508 the average voltage of subdivisions in the battery. The average value may be used to calculate a ratio at 510 of the electrical parameter of the subdivisions satisfying the criterion to the average electrical parameter of the battery pack. According to various embodiments, the ratio may then be multiplied by the average value per subdivision of the electrical parameter battery, or then may be multiplied by the value of the total electrical parameter.

At 514, measurements may be synchronized based upon a time delay between an electrical characteristic associated with the one or more subdivisions in the battery that satisfy the criterion and the same electrical characteristic associated with the one or more subdivisions that do not satisfy the criterion. For example, in an embodiment in which the criterion is set to identify the subdivision having the lowest capacity, at 514, method 500 may determine a time delay between a minimum or maximum voltage associated with the subdivision having the lowest capacity and the minimum or maximum average voltage of the battery system as a whole. At 516, the time delay determined at 514 may be utilized to synchronize the electrical parameters.

At 518, the synchronized and scaled voltage and current measurements associated with a weak subdivision (e.g., the weakest sub-pack or cell) may be utilized by a battery state estimator. According to some embodiments, the battery state estimator may estimate a state of charge associated with the weakest sub-pack or cell. A battery control system may utilize the estimated state of charge in order to control, among other things, the discharge from the battery. The battery control system may, for example, restrict further discharge from a battery in order to prevent against over-discharging the weakest cell and/or sub-pack in the battery.

In certain embodiments, the systems and methods disclosed herein may be implemented, at least in part, using one or more computer systems. For example, certain features and functionality of the battery control system, vehicle computer system, and/or external computer system may be implemented using a computer system. The systems and methods disclosed herein are not inherently related to any particular computer or other apparatus and may be implemented by a suitable combination of hardware, software, and/or firmware. Software implementations may include one or more computer programs comprising executable code/instructions that, when executed by a processor, may cause the processor to perform a method defined at least in part by the executable instructions. The computer program can be written in any form of programming language, including compiled or interpreted languages, and can be deployed in any form, including as a standalone program or as a module, component, subroutine, or other unit suitable for use in a computing environment. Further, a computer program can be deployed to be executed on one computer or on multiple computers at one site or distributed across multiple sites and interconnected by a communication network. Software embodiments may be implemented as a computer program product that comprises a non-transitory storage medium configured to store computer programs and instructions that, when executed by a processor, are configured to cause the processor to perform a method according to the instructions. In certain embodiments, the non-transitory storage medium may take any form capable of storing processor-readable instructions on a non-transitory storage medium. A non-transitory storage medium may be embodied by a compact disk, digital-video disk, a magnetic tape, a Bernoulli drive, a magnetic disk, a punch card, flash memory, integrated circuits, or any other non-transitory digital processing apparatus memory device.

Although the foregoing has been described in some detail for purposes of clarity, it will be apparent that certain changes and modifications may be made without departing from the principles thereof. For example, in certain embodiments, the state of charge sensors may be configured to also incorporate features allowing measurement of internal battery section resistances. Similarly, the battery control system may be configured to incorporate certain features and/or functionality of the cell balancing system. Similarly, certain features of the embodiments disclosed herein may be configured and/or combined in any suitable configuration or combination. Additionally, certain systems and/or methods disclosed herein may be utilized in battery systems not included in a vehicle (e.g., a backup power battery system or the like). It is noted that there are many alternative ways of implementing both the processes and apparatuses described herein. Accordingly, the present embodiments are to be considered illustrative and not restrictive, and the invention is not to be limited to the details given herein, but may be modified within the scope and equivalents of the appended claims.

The foregoing specification has been described with reference to various embodiments. However, one of ordinary skill in the art will appreciate that various modifications and changes can be made without departing from the scope of the present disclosure. For example, various operational steps, as well as components for carrying out operational steps, may be implemented in alternate ways depending upon the particular application or in consideration of any number of cost functions associated with the operation of the system. Accordingly, any one or more of the steps may be deleted, modified, or combined with other steps. Further, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced, are not to be construed as a critical, a required, or an essential feature or element.

As used herein, the terms "comprises" and "includes," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus.

Those having skill in the art will appreciate that many changes may be made to the details of the above-described embodiments without departing from the underlying principles of the invention. The scope of the present invention should, therefore, be determined only by the following claims.

The invention claimed is:

1. A system comprising:
a battery pack comprising a plurality of subdivisions;
a measurement system configured to determine a plurality of subdivision electrical parameters, each subdivision electrical parameter of the plurality of electrical parameters being associated with one of the plurality of subdivisions, and to determine a pack electrical parameter associated with the battery pack;
a battery control system communicatively coupled to the measurement system, the battery control system configured to identify a subdivision satisfying a criterion based on the plurality of subdivision electrical parameters and generate an adjusted pack electrical parameter based on the electrical parameter of the identified subdivision and the pack electrical parameter; and
a battery state estimation system in communication with the battery control system, the battery state estimation system configured to generate an estimated battery state based on the adjusted pack electrical parameter;
wherein the battery control system is further configured to determine a ratio of the subdivision electrical parameter of the identified subdivision and the pack electrical parameter, and to scale the pack electrical parameter by the ratio to generate the adjusted pack electrical parameter.

2. The system of claim 1, wherein the battery control system is further configured to measure a time delay between one of a maximum value and a minimum value of the subdivision electrical parameter of the identified subdivision and a corresponding maximum or minimum value of the pack electrical parameter, to provide the time delay to the battery state estimation system; and
wherein the battery state estimation system is further configured to generate the estimate of the voltage of the battery pack based on the time delay.

3. The system of claim 1, wherein each of the plurality of subdivisions is individually replaceable, and wherein the battery pack comprises at least one replacement subdivision.

4. The system of claim 1, wherein the battery control system is configured to identify one of a lowest capacity subdivision, a lowest voltage subdivision, and a lowest current subdivision based on the criterion.

5. The system of claim 1, wherein the measurement system further comprises a plurality of voltage measurement sensors, and the subdivision electrical parameter comprises a voltage associated with each of the plurality of subdivisions.

6. The system of claim 1, wherein the estimated battery state comprises a state of charge of the identified subdivision, and the battery control system is further configured to restrict discharge from the battery pack when the estimated state of charge falls below an over-depletion threshold.

7. The system of claim 1, wherein each of the plurality of subdivisions comprises one or more battery cells.

8. The system of claim 1, wherein each of the plurality of subdivisions comprises one or more battery sub-packs, and each of the one or more battery-sub packs comprises one or more battery cells.

9. A method of estimating the voltage of a battery pack comprising a plurality of subdivisions, the method comprising:
determining a plurality of subdivision electrical parameters, each subdivision electrical parameter of the plurality of electrical parameters being associated with one of the plurality of subdivisions;
identifying a subdivision satisfying a criterion based on the plurality of subdivision electrical parameters;
determining a pack electrical parameter associated with the battery pack;
generating an adjusted pack electrical parameter based on the subdivision electrical parameter of the identified subdivision and the pack electrical parameter;
providing the adjusted pack electrical parameter to a battery state estimation system;
generating an estimated battery state based on the adjusted pack electrical parameter;
determining a ratio of the subdivision electrical parameter of the identified subdivision and the pack electrical parameter; and
scaling the pack electrical parameter by the ratio to generate the adjusted pack electrical parameter.

10. The method of claim 9, further comprising:
measuring a time delay between a one of a maximum value and a minimum value of the subdivision electrical parameter of the identified subdivision and a corresponding maximum or minimum value of the pack electrical parameter; and
providing the time delay to the battery state estimation system;
wherein generating the estimated battery state is further based on the time delay.

11. The method of claim 9, wherein each of the plurality of subdivisions is individually replaceable, and wherein the battery pack comprises at least one replacement subdivision.

12. The method of claim 9, wherein identifying the subdivision satisfying the criterion comprises identifying one of a lowest capacity subdivision, a highest electrical resistance, a lowest voltage subdivision, and a lowest current subdivision.

13. The method of claim 9, wherein the subdivision electrical parameter comprises a subdivision voltage and the adjusted pack electrical parameter comprises an average voltage.

14. The method of claim 9, wherein the estimated battery state comprises an estimated state of charge.

15. The method of claim 14, further comprising restricting discharge from the battery pack when the estimated state of charge falls below a threshold.

16. The method of claim 9, wherein each of the plurality of subdivisions comprises one or more battery cells.

17. The method of claim 9, wherein each of the plurality of subdivisions comprises one or more battery sub-packs, and each of the one or more battery-sub packs comprises one or more battery cells.

18. A system comprising:
a battery pack comprising a plurality of subdivisions;
a measurement system configured to determine a plurality of subdivision electrical parameters, each subdivision electrical parameter of the plurality of electrical parameters being associated with one of the plurality of subdivisions, and to determine a pack electrical parameter associated with the battery pack;
a battery control system communicatively coupled to the measurement system, the battery control system configured to identify a subdivision satisfying a criterion based on the plurality of subdivision electrical parameters and generate an adjusted pack electrical parameter based on the electrical parameter of the identified subdivision and the pack electrical parameter; and a battery state estimation system in communication with the battery control system, the battery state estimation system configured to generate an estimated battery state based on the adjusted pack electrical parameter;

wherein the battery control system is further configured to measure a time delay between one of a maximum value and a minimum value of the subdivision electrical parameter of the identified subdivision and a corresponding maximum or minimum value of the pack electrical parameter, to provide the time delay to the battery state estimation system; and wherein the battery state estimation system is further configured to generate the estimate of the voltage of the battery pack based on the time delay.

* * * * *